United States Patent
Haley et al.

(10) Patent No.: US 6,481,263 B1
(45) Date of Patent: Nov. 19, 2002

(54) HAND-HELD DETECTION SYSTEM USING GC/IMS

(75) Inventors: Lawrence V. Haley, Ottawa; Govindanunny Thekkadath, Nepean, both of (CA)

(73) Assignee: Intelligent Detection Systems, Inc., Nespean (CA)

( * ) Notice: Subject to any disclaimer, the term of this patent is extended or adjusted under 35 U.S.C. 154(b) by 0 days.

(21) Appl. No.: 09/622,074

(22) PCT Filed: Feb. 10, 1999

(86) PCT No.: PCT/US99/02837
§ 371 (c)(1),
(2), (4) Date: Sep. 28, 2000

(87) PCT Pub. No.: WO99/41601
PCT Pub. Date: Aug. 19, 1999

Related U.S. Application Data (60) Provisional application No. 60/074,431, filed on Feb. 11, 1998.

(51) Int. Cl.[7] ............................. G01N 1/00; B01D 59/44
(52) U.S. Cl. ........................................ 73/23.41; 250/287
(58) Field of Search ............................. 73/23.41, 23.42, 73/23.2; 250/287; 422/78

(56) References Cited

U.S. PATENT DOCUMENTS

| | | | |
|---|---|---|---|
| 5,092,218 A | 3/1992 | Fine et al. | 86/50 |
| 5,135,549 A | 8/1992 | Phillips et al. | 95/8 |
| 5,147,611 A | 9/1992 | Stout et al. | 422/78 |
| 5,153,673 A | 10/1992 | Amirav | 356/315 |
| 5,189,301 A | 2/1993 | Thekkadath | 250/287 |
| 5,268,302 A | 12/1993 | Rounbehler et al. | 436/96 |
| 5,338,931 A | 8/1994 | Spangler et al. | 250/287 |
| 5,345,809 A | 9/1994 | Corrigan et al. | 73/23.2 |
| 5,856,616 A | 1/1999 | Maswadeh et al. | 73/23.42 |
| 6,171,378 B1 | 1/2001 | Manginell et al. | 96/143 |
| 6,239,428 B1 | 5/2001 | Kunz | 250/287 |

FOREIGN PATENT DOCUMENTS

| | | | |
|---|---|---|---|
| WO | 99/21212 | 4/1999 | H01J/49/04 |

*Primary Examiner*—Hezron Williams
*Assistant Examiner*—Jay L Politzer
(74) *Attorney, Agent, or Firm*—Ernest D. Buff; Gordon E. Fish; Ernest D. Bugg & Associates LLC (57) ABSTRACT

A sampling and gas chromatographic separation detection system and method which is capable of sampling and analyzing particulate and vapors containing drug and explosive residues in real time. The system and method provide high speed and low power consumption from the combination of a cold ion mobility spectrometer (IMS) with a "heat-on-demand" gas chromatographic (GC) system which eliminates the need to continuously heat the device, thus making the detection system battery operable and portable.

20 Claims, 5 Drawing Sheets

HAND-HELD DETECTION SYSTEM USING GC/IMS

CROSS-REFERENCE TO RELATED APPLICATIONS

The following patent application is based on and claims the benefit of U.S. Provisional Patent Application Ser. No. 60/074,431 filed Feb. 11, 1998.

DESCRIPTION

FIELD OF THE INVENTION

The present invention relates generally to detection and analysis of gaseous components and more particularly to a hand-held detection system using gas chromatography and/or ion mobility spectrometer.

BACKGROUND OF THE INVENTION

Figure 1A:
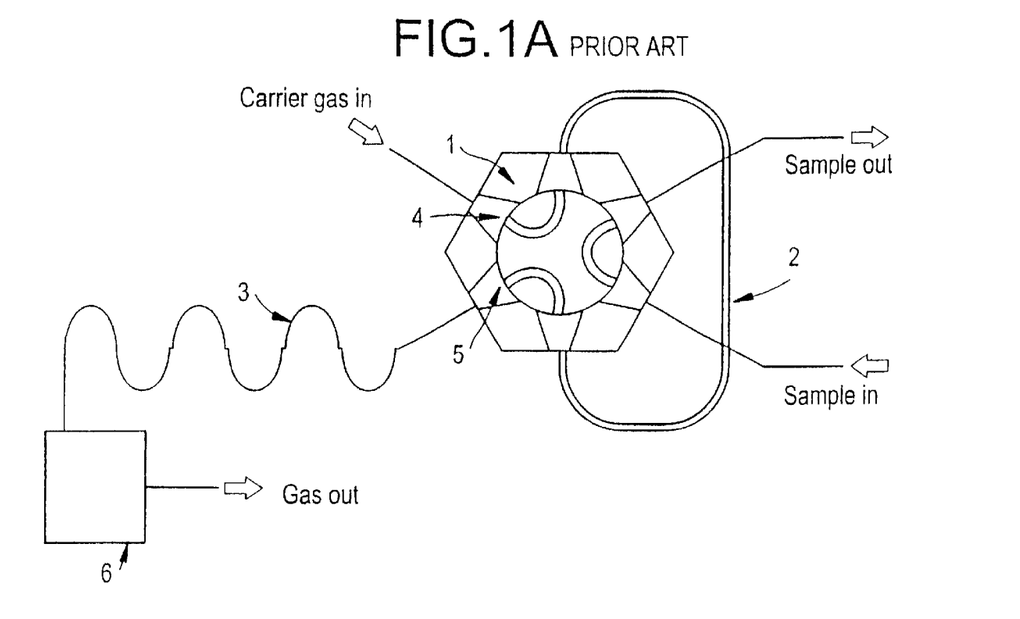
FIGS. 1a and 1b illustrate a prior art system for separating the components of a gaseous mixture as the mixture flows through a tubular column.
Figure 1B:
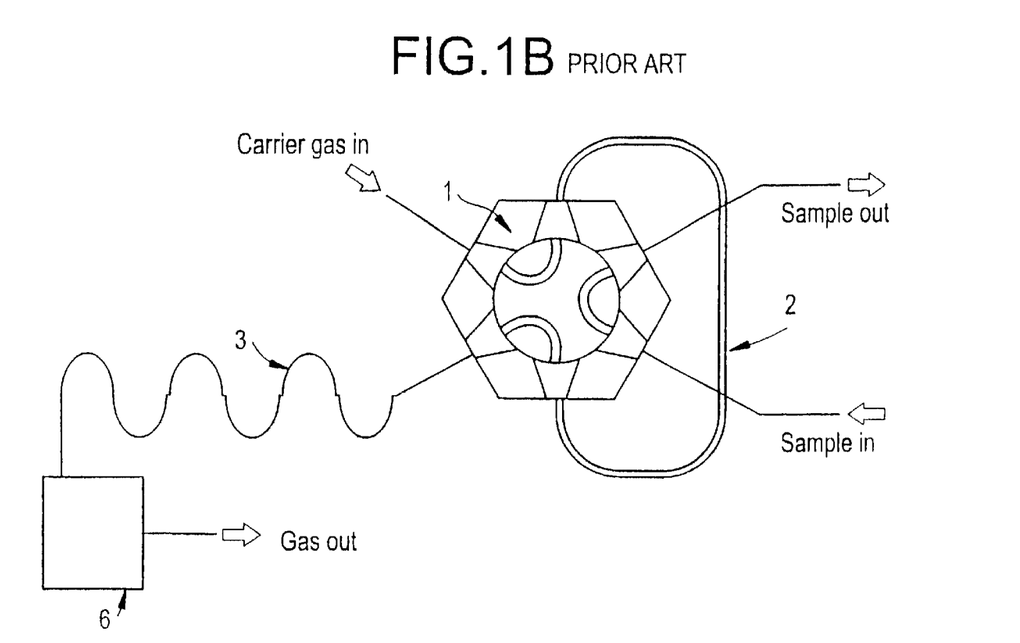

Gas chromatography is an established analytical technique for separating the components of a gaseous mixture as the mixture flows through a tubular column. There are many different ways of injecting the initial sample into the column and performing the separation. For example, one way of carrying out the separation in open tubular columns is shown in FIGS. 1a and 1b. In this method, valve 1 admits a small volume of the sample flowing through the loop 2 into the column 3 when the valve is switched from the sampling position shown in FIG. 1a to the injection position shown in FIG. 1b. This volume of sample is then carried down the column by a flow of carrier gas through the port 4 and 5 of the valve and separated into its components when it interacts with the column wall coated with the appropriate separating medium. The net result is that the components exit the column as separate volumes at different times. The time between the injection and the exit of a component is called its retention time. The components are detected by an appropriate detection system, for example, an electron capture detector (ECD) or a thermal conductivity detector. The signal generated by the detector (the chromatogram) can then be plotted out for analysis.

The speed at which analysis takes place in this system is dependent on several factors including the type and length of the column, its temperature and the velocity of the carrier gas in the column. In general total analysis times are in the order of minutes to hours. Sample preparation and injection can take several minutes to hours depending on the nature of the sample. Thus for real time analysis this process needs to be speeded up considerably.

Real time analysis is highly desirable when using the technique of gas chromatography for quickly detecting and identifying compounds contained in narcotics and explosives. Then sampling and detection systems based on gas chromatography can be used for checking suspicious objects which could contain explosive devices or controlled drugs and narcotics. Such devices are useful at border crossings and airports for identifying and preventing drug smuggling or terrorist activity. Therefore, it is also highly desirable to make such detection system portable and operable in real time.

Moreover, it is also desirable to make such systems battery operable. Gas chromatography of drug or explosive samples require that the sampling separation systems work at high temperatures typically in the region of 100 to 300 degrees Celsius. Presently, there are no energy efficient or portable GC-IMS devices which can operate in the high temperature regime for analyzing drugs or explosives because power requirements for gas chromatography systems usually preclude battery operated portable systems of practical size and weight. Therefore, it is also highly desirable to have a gas chromatography system with minimum power consumption without sacrificing performance.

SUMMARY OF THE INVENTION

The present invention provides a novel design and method of operation for a pulsed high speed sampling and gas chromatographic (GC) separation system which is capable of sampling and analyzing particles and vapors containing drug and explosive residues in less than twenty seconds and which at the same time consume very little power. The speed and power savings provided by the present invention uses a heat-on-demand (HOD) technology explained below.

There are several important advantages for using the pulsed analysis technique in simple, portable, low power GC-IMS sample gathering and analytical system as disclosed by the present invention. Because of the pulsed nature of the system, power consumption takes place only when the system is analyzing, greatly increasing the overall energy efficiency of the system compared to static systems where the components are always maintained at high operating temperatures. This makes its use practical in hand-held analytical devices using batteries as power sources.

Moreover, the pulsed heating sequence avoids the use of valves to switch a sample packet into the column as is done in static high temperature systems, making the system simpler and more reliable.

Advantageously, the system of the present invention operates as one integrated system for sample gathering, analysis, and data presentation, thus, making it an ideal portable real-time analytical instrument for many applications, including drug and explosive checks and searches at border points, airports, etc., and also for air quality monitoring.

Furthermore, the present invention utilizes an ion mobility spectrometer (IMS) device as a second analyzer. using the IMS greatly increases the overall selectivity and sensitivity of the instrument without adversely affecting its performance or energy efficiency. In the present invention the IMS device is preferably a "cold" IMS device which deliberately operates at a temperature low enough such that the sample vapors introduced into the IMS actually condense in the IMS in a fraction of a second after their introduction. The deliberate trapping of the vapors in the IMS effectively removes the sample from the ionization process because after condensation, the vapor pressure of the compound at the operating temperature of the IMS is so low as to be negligible. Since the compound is no longer present in the vapor form, ion production no longer takes place at a sufficient rate as to be detectable. The process of sample introduction in such a cold IMS is different from sample introduction in conventional IMS devices. The sample is first transported in the vapor form to the entrance of the reaction region at a temperature several tens of degrees higher than the temperature of the reaction region and the temperature of the carrier gas flowing in the reaction region. As the sample vapor enters the reaction region, it encounters the colder gas in the region and starts to cool down. Before the cooling takes place, however, the reactant ions present in the reaction region rapidly convert a portion of the vapor sample into product ions which are subsequently swept away by an electric field into a drift region. The rest of the sample condenses on the walls of the reaction region and is no longer available for ionization reactions in the vapor phase.

The IMS of the instant invention operates at essentially constant temperatures. As a result, the combination of the cold IMS and the "heat-on-demand" gas chromatographic (GC) separation system of the present invention greatly eliminates the power requirements needed for keeping the device continuously heated, thus making the system ideal as a battery operable portable detection device.

Furthermore, the combination of the cold IMS and the "heat-on-demand" gas chromatographic (GC) separation system of the present invention is encased in a portable closure so that it may be hand-carried and ported easily. Moreover, the case preferably includes a display portion where a display device may be attached to provide information regarding the samples detected.

Further features and advantages of the present invention as well as the structure and operation of various embodiments of the present invention are described in detail below with reference to the accompanying drawings. In the drawings, like reference numbers indicate identical or functionally similar elements.

BRIEF DESCRIPTION OF THE DRAWINGS

Preferred embodiments of the present invention will now be described, by way of example only, with reference to the accompanying drawings in which.

DETAILED DESCRIPTION OF THE PREFERRED EMBODIMENT OF THE INVENTION

In the preferred embodiment, the valveless gas chromatographic system of the present invention is an integrated sampling and analysis device which is preferably used with an ion mobility spectrometer operating at room temperature. The ion mobility spectrometer is described in a commonly owned PCT Application No. PCT/US98/22092 entitled A SAMPLE TRAPPING ION MOBILITY SPECTROMETER FOR PORTABLE MOLECULAR DETECTION, filed on Oct. 20, 1998, the description of which is fully incorporated herein by reference thereto.

Figure 2A:
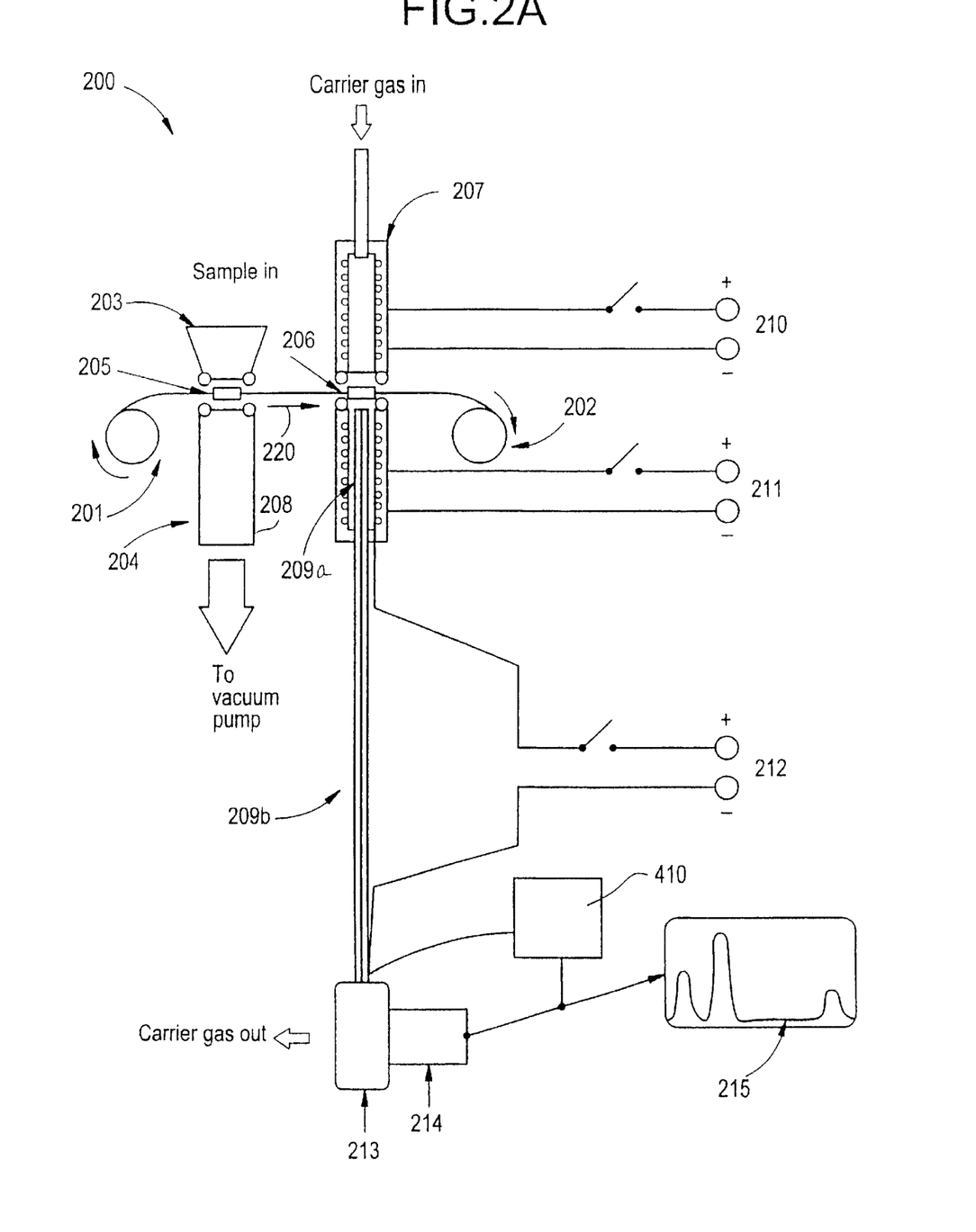
FIG. 2a illustrates a schematic diagram of the valveless gas chromatographic system of the present invention.

FIG. 2a shows a schematic diagram of the system of the present invention. The system may be divided into a sampling section and analysis section. The system includes a sample trap having a ribbon about half an inch wide wound on bobbins 201 and 202 and passing between the sampling and analysis sections. The material used to make the ribbon may be a metallic mesh typically of size 400 or more or other porous type which allows air to pass through freely but traps small particles and vapors. The vapor trapping or collecting ability may be increased by coating the ribbon with an absorbing media known in the art for use in absorbing the desired molecules of interest.

A nozzle 203 and a pump tube 204 are cylindrical entities with soft O ring seals at the ends that are closer to the ribbon. When the machine is in the sampling mode, 203 and 204 form a tight seal on portion 205 of the ribbon. A vacuum pump attached to the pump tube 204 sucks vapors and/or particles through the sampling nozzle 203 onto the sampling area 205 of the ribbon. After a predetermined time duration of sampling, e.g., few seconds of sampling, the nozzle 203 and the pump tube 204 are moved away from the ribbon to break the seal. The moving process is accomplished with the aid of electric motors controlled by a computer 410. After the seal is broken, the ribbon is moved in the direction shown by the arrow 220 to the location at 206. The movement of the ribbon is also accomplished with the aid of electric motors and position sensors which stop the motors after positioning the sample.

Once at position 206, the desorption port 207 and the injection port 208 move towards the ribbon under motor control and form an air-tight seal around 206. The desorption port 207 is a cylindrical entity less than ¼" in diameter, and made include a built-in electric heater 210 to heat the gas passing through the ribbon to a temperature of 200 Celsius or more within a few seconds. A carrier gas flows into 207 and gets heated by the heaters so that when the hot gas exits out of the desorption port 207 and impinges on portion 206 of the ribbon, it in turn heats the sample trapped in the ribbon at 206. The rate of flow of the carrier gas is typically about 50 to 200 cc/min.

At the time the desorption port 207 is hot, the injection port 208 is also heated to the same temperature using the same technique as for the desorption port 207 with the aid of electric heater 211. The injection port 208 has a more complex construction because it has the gas chromatographic column 209 attached in a unique manner. The column 209 in the preferred embodiment has a metallic jacket which is directly heated by passing a current through it from a controlled source 212. Portion 209a of the column 209 is inside the injection port 208 and portion 209b is outside the injection port 208. The far end of 209b is connected to the detector 213. This detector 213 is preferably an IMS detector. The carrier gas flowing into the injection port 208 goes directly into portion 209a of the column and thence into portion 209b. When the desorption port 207 and the injection port 208 are heated, the column 209 is not heated. This causes the vapors of the trapped sample at 206 which are released by the hot carrier gas to move through portion 209a of the column and condense at the beginning of portion 209b of the column.

Once the sample has settled down in the front end of the column 209, the heaters 210 and 211 are switched off, typically by a computer controller 410. The temperature of the heaters rapidly drop to ambient in a few seconds because the ports 207, 208 are constructed with the minimum amount of heat capacity. The computer 410 senses the temperature of the ports 207, 208 and when they have reached an appropriate minimum value which is preferably about 20 degrees Celsius above the ambient, the computer 410 turns on the heater 212. This causes the column portions 209a, 209b to heat up rapidly from ambient to more than 200 degrees Celsius in a few seconds. The rate of this heating is controlled by the computer program. Since there is a carrier gas flow in the column during the heating cycle, the condensed compounds move down the column and separate into the individual components and exit into the IMS 213 at different times. The IMS ionizes these packets of individual components in the sample and further separate the components according to their mobility in the drift gas flowing in the IMS. The individual ion packets are then collected on an electrode and amplified electronically by amplifier 214 for further signal processing and display 215 using the computer 410. It should be noted that detection devices other than IMS may be used, e.g., by attaching a different detection device at the end of the column 209.

Figure 2B:
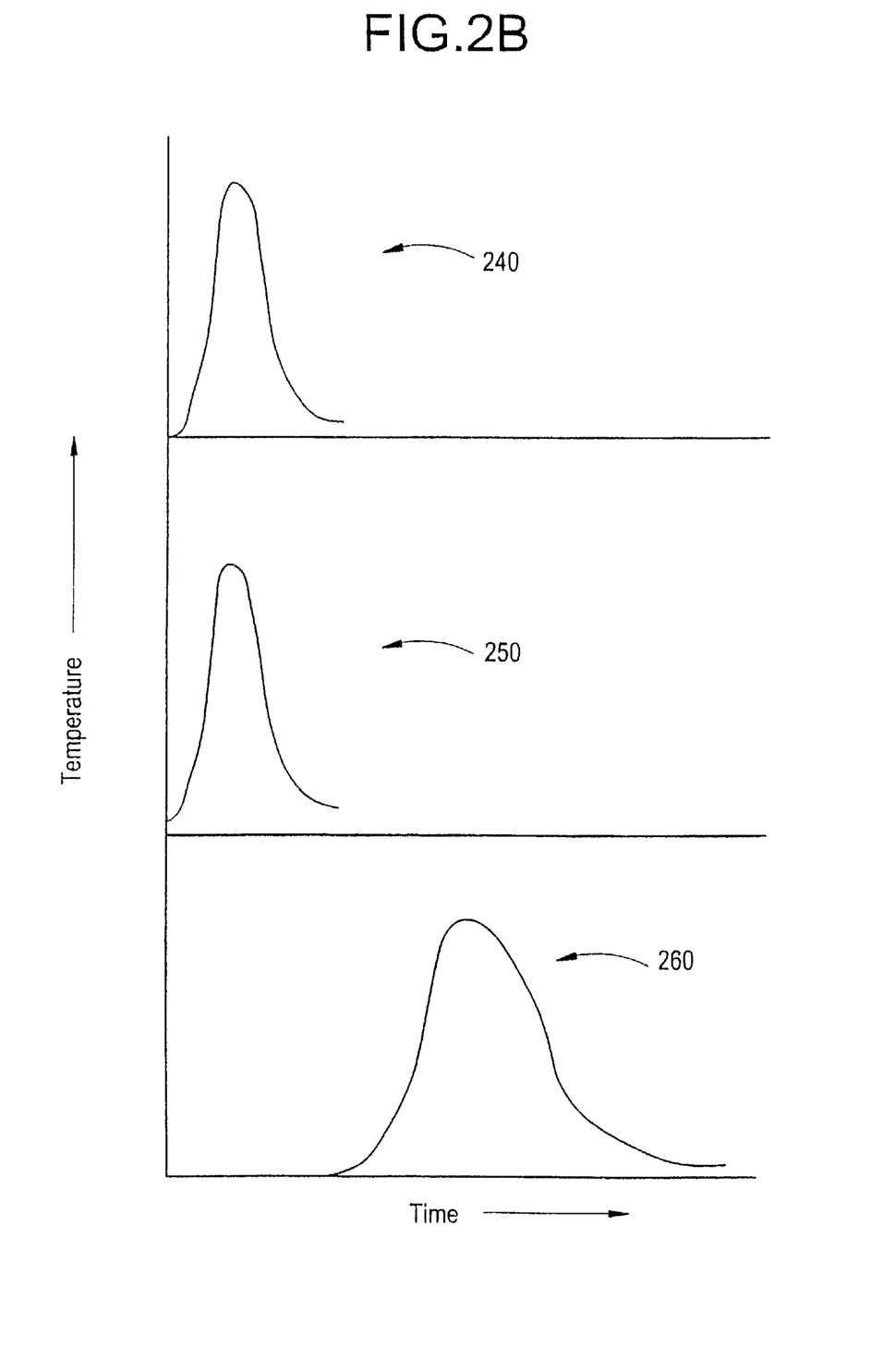
FIG. 2b illustrates a graphical representation of the heating and cooling sequence of the present invention.

The sequence of heating and cooling of the analysis system is critical to the success of the device as a programmed pulsed gas chromatographic system. A graphical representation of the heating and cooling sequence is shown in FIG. 2b where the horizontal axis is the time axis common to the three graphs. The three separate vertical axes are the temperature axes. The maximum value of the temperatures depend on the nature of the compounds being analyzed, and is typically around 200 degrees Celsius for explosive and drug compounds. The rate of rise and fall of the temperature programming of the column is in general constant, but can be changed to follow a desired curve using the computer 410 to control the duty cycle of the heater. As shown in FIG. 2b, there is no delay between the heating cycles 240, 250 of the heaters in the ports 207, 208, but the column heating starts as shown at 260 after these heaters have cooled down, to achieve the desired effect described above.

In addition, the heated portions have low heat capacities and are designed to dissipate the heat efficiently. Such a design is important for achieving fast analysis times. With the system of the present invention as described above, the ports 207, 208 and the column 109 can be heated and cooled over the working range in a few seconds.

Figure 3:
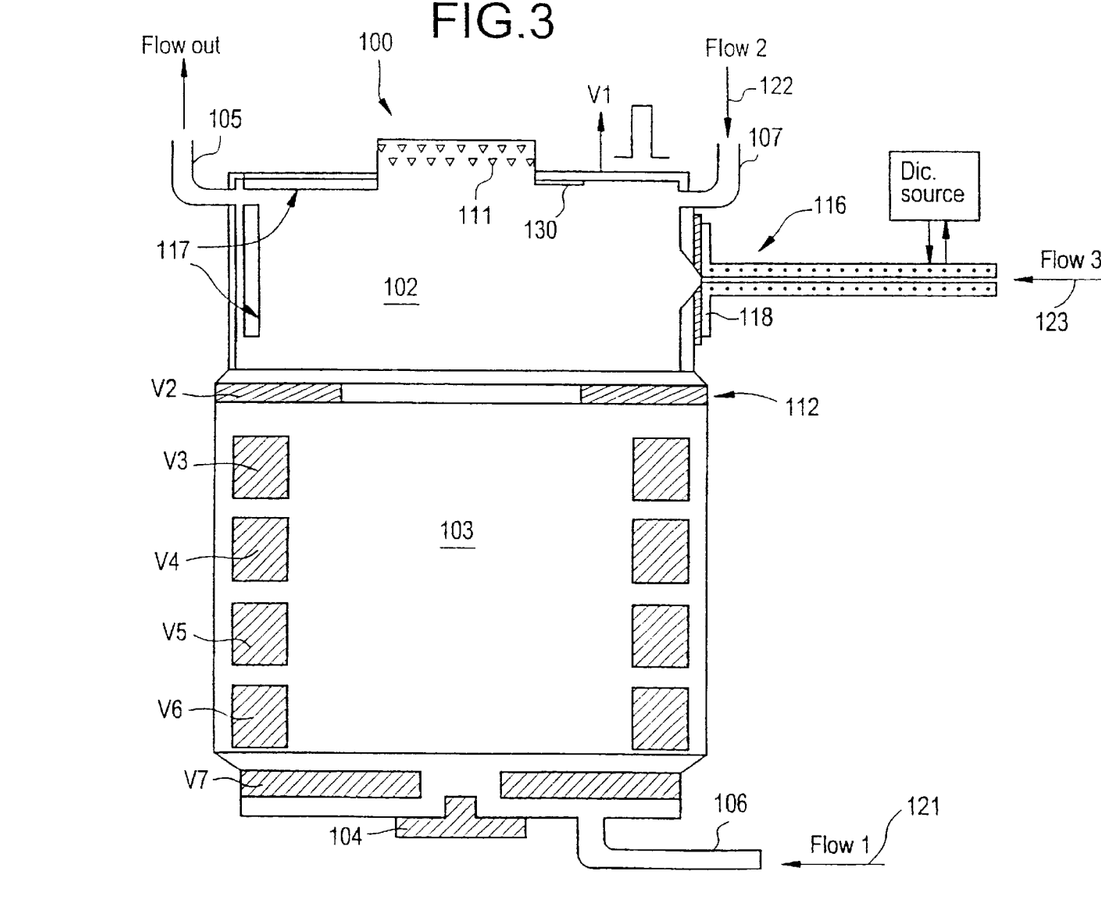
FIG. 3 is an illustrative cross-sectional view of the low power IMS device according to the invention.

In the preferred embodiment, the valveless gas chromatographic system of the present invention is integrated with a cold ion mobility spectrometer operating at room temperature. FIG. 3 depicts the process of sample introduction and ionization in the cold IMS device 100 of the invention. AS shown in FIG. 3, the reaction region 102 is essentially cylindrical having an ionizing source 111 at one end of the cylinder and an electrode assembly 112 at the other end of the cylinder for creating an electric field that will transport the ions to the drift region 103. Additionally shown are two gas inlet ports 106, 107 and a gas outlet port 105. Preferably, there are three gas flows into the reaction region. A first gas flow 121 input from gas inlet port 106 is the drift gas flow comprising a buffer gas such as air or nitrogen which starts at the detector end 104 of the IMS 100 and flows into the reaction region 102 and out through the gas outlet port 105. In the preferred embodiment, a drift gas flow rate is of a value required to keep the drift region free of any unwanted vapors and to provide a constant background buffer gas for the ions to drift in. For example, this drift gas flow rate may be about 10 cc/min. A second gas flow 122 input from gas inlet port 107 provided near the top end of the reaction region 102 has a dual purpose: 1) for carrying the reactant gas which is required to provide an efficient reaction pathway for the sample species; and, 2) for functioning as an "air curtain" to prevent the condensing sample species from condensing on the ionization source end. The exit of this gas flow is additionally via the outlet port 105. A third flow 123 is the sample flow containing vapors of the sample substance. The sample inlet 116 for receiving and directing the sample gas flow 123 is normally at the same temperature as the reaction region 102 and the gas flowing into the inlet has the same temperature as that of the other two gas flows 121, 122. However, according to the invention, when the sample injection takes place, the inlet tube 116 is heated to bring its temperature up. FIG. 3 illustrates a pulsed direct current source 125 for heating the sample inlet 116. The temperature to which the sample inlet port 116 is heated preferably is a function of time and the nature of the sample. For example, when analyzing the drugs cocaine and heroin, the temperature may be ramped from about 50° C. to about 230° C. in six seconds. The ramp is typically proportional to the square of the time elapsed but in general is a function programmed into the computer including a steady temperature (usually 180° C). The inlet tube is designed in such a way that there are no cold spots on it, especially at the location 118 where the inlet tube 116 joins the reaction region. When the temperature of the sample inlet tube 116 is high enough, the vapors of the sample, e.g., drugs, get efficiently transported into the reaction region 102 without condensing on the walls of the inlet tube. The inlet tube is then cooled rapidly, i.e., the heat source is removed within seconds, to prevent any further injection of the sample into the reaction region.

The sample vapor in the reaction region 102 is then subjected to reactions with the charged species present in the region 102. The nature of the reactions and their ionization rates depend upon the ionizing species from the ionizing source 111, and the compound being ionized. In general, the reactions occur on a time scale in the order of microseconds, with the sample vapors still in their vapor state. Condensation of the vapors on the walls of the tube starts to take place only after several tens of milliseconds after their introduction into the reaction region 102 and may be varied by adjusting the flow rates of the various gas streams in the reaction region.

In the preferred embodiment, after a sufficient number of product ions have accumulated in the reaction region, an electric field of the correct polarity and magnitude is established between the reaction 102 and drift regions 103 to pulse the ions into the drift region. This pulse V1 is typically applied to the electrode 111 with respect to the voltage V2 on electrode 112 and has a relative amplitude with respect to V2 of several hundred volts and a duration of 200 to 500 microseconds. This creates an ion packet to be injected into the drift region. The constituents of the ion packet are separated by their mobility in the drift region as in any IMS device, typically using an electric field created by ring electrodes at different potentials indicated as V3, V4, . . . , V7 in FIG. 3. The detection of the separated ion packets can also be done conventionally as in a typical IMS or can be injected into other apparatus using electric fields for further processing. It should be noted that ion injection into the drift region 103 may also be carried out using the Nielson-Bradbury shutter 125 as shown in the conventional IMS device.

If the sample to be analyzed has a substantial vapor pressure at room temperature, the sample may be removed from the reaction region 102 by cooling the reaction region 102 and keeping its temperature lower than the temperature of the sample. Means for cooling the reaction region 102 may include thermo-electric cooling or, using maintaining a drift gas 121 at a cooler temperature. This temperature reduction reduces the vapor pressure of the sample in the reaction region to a low enough value so as to be negligible for producing measurable quantities of ions, as required by the invention. Another way of achieving this is to provide absorbing media 130 for the sample vapor on the inside walls of the reaction region such as shown in FIG. 3. Once the sample reaches the absorber, it is trapped and the net effect is the same as a lowering of the sample temperature, and thus its vapor pressure.

The sample inlet drive 116 shown in FIG. 3 is normally used in a pulsed mode in order to reduce the loading of the reaction region with too much sample. The inlet tube 116 comprises a gas chromatographic column which normally sits at a low temperature so that the sample is trapped at the inlet end of the column. The column may then be heated at a certain rate using a pulsed direct electric current through the column if it is metallic or by an indirect means, e.g., infra-red or hot air envelope, if it is non-metallic. This causes the sample to travel down the column into the drift region of the IMS for analyzation as described above. Since the constituents in the sample are separated by the column, the IMS analyzes each constituent at a different time and thus the IMS mobility spectra will vary in time. Once the sample is analyzed, the column is rapidly cooled and prepared for trapping the next sample in the column.

Since the reaction region 102 acts as a condensing location for the sample, it eventually becomes loaded with the condensed sample and becomes unusable. The reaction region electrode 111 is made to have an inner condensing liner 117 which, when loaded with sufficient sample residue, can easily be replaced with a new one. Under normal circumstances of sampling, replacement of the inner condensing liner 117 may occur only after several thousand hours of operation since each sample is only a few ten to a few hundred nanograms in weight.

Figure 4:
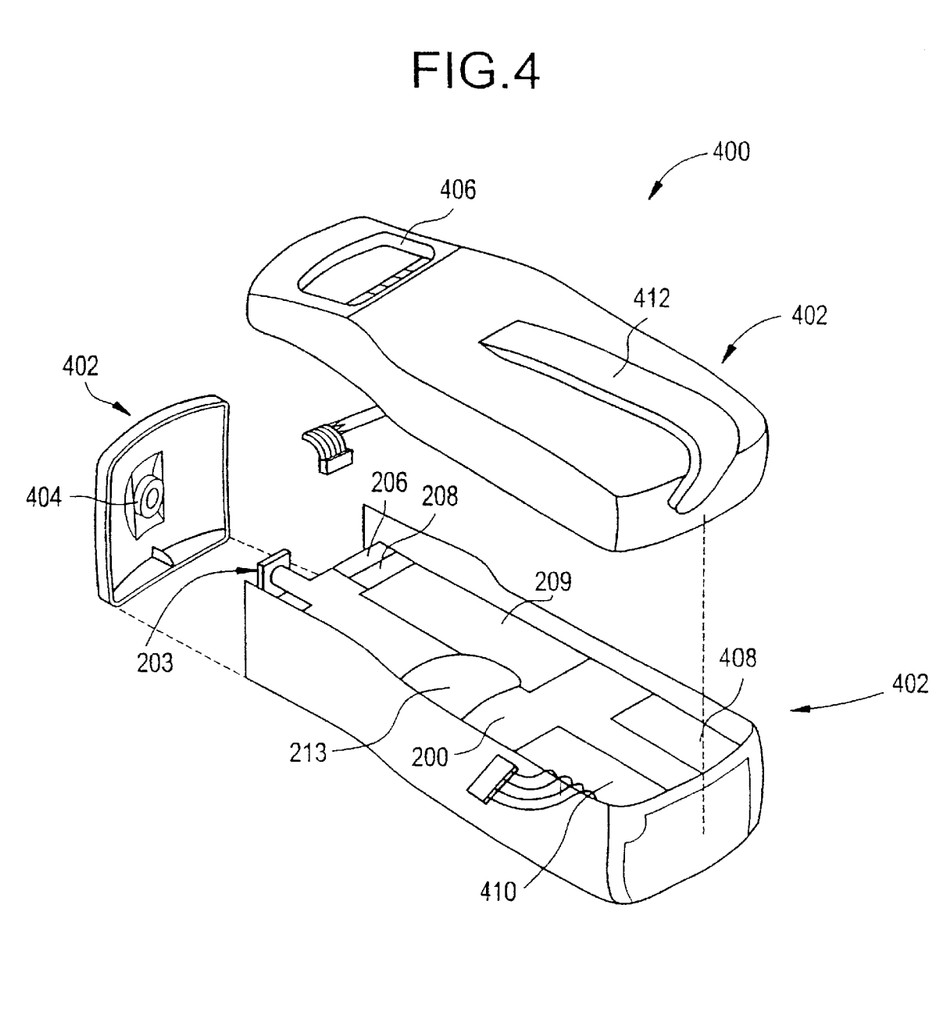
FIG. 4 is illustrates the system of the present invention adapted to a hand held portable case.

In the preferred embodiment, the system of the present invention having the combination of the "heat-on-demand" gas chromatographic (GC) separation system and the cold IMS as described above is encased in a portable closure structure, an example of which is shown in FIG. 4. When integrated in a portable case as shown, it may be hand-carried while in use and ported easily from one place to another. Moreover, the case preferably includes a display portion where a display device may be attached to provide information regarding the samples detected.

FIG. 4 illustrates an open view 400 of an example of a case 402 with a handle 412, for containing the detection system of the present invention. As shown, the GC/IMS detection system 200 of the present invention is adapted inside the case 402. A computer controller 410 for controlling the heating sequences as well as the display device 406 is also shown in FIG. 4. The case includes an opening 404 where the nozzle 203 (FIG. 2a) part of the gas chromatographic system 200 coincides for receiving the samples to be detected. A pump 408 is connected to the pump tube 204 (FIG. 2) for sucking the sample particles onto the ribbon (FIG. 2). Depending on how and from where the sample is being taken, the opening 404 at the outer side of the case 402 may be connected with any known collecting apparatus such as a vacuum brush. As shown, a portion of the case 402 includes a screen display 406 for displaying the sample information processed by the system of the present invention. optionally, a keyboard may be included with the display device. Moreover, the case 402 may include an audio device (not shown) for alerting users as necessary. The case 402 also includes a power supply unit (not shown) which includes batteries and optionally an AC adapter.

While the invention has been particularly shown and described with respect to a preferred embodiment thereof, it will be understood by those skilled in the art that the foregoing and other changes in form and details may be made therein without departing from the spirit and scope of the invention.

We claim:

1. A portable high speed sampling and gas chromatographic separation system which is capable of sampling and analyzing molecules of interest, the system comprising:
   an input device for collecting sample particles having the molecules of interest at a first position;
   a port device capable of being heated by a heat pulse, the port device connected to the input device to receive sample particles having the molecules of interest at a second position, the molecules of interest releasing a vapor in response to the heat pulse applied to the port device;
   a gas column device connected to the port device, the gas column device receiving the vapor, the gas column device having a temperature lower than the port device, wherein the vapor is condensed in the gas column device, the gas column device further capable of being heated by a heat pulse, wherein in response to the heat pulse applied to the gas column, the condensed vapor of the molecules of interest separate into individual components and exit the gas column at different times; and
   a detector connected to the gas column device, the detector receiving the individual components of the condensed vapor, the detector for analyzing the molecules of interest.

2. The system as claimed in claim 1, wherein the port device includes:
   a desorption port for receiving a carrier gas, the desorption port capable of being heated by a heat pulse and further heating the carrier gas in response to the heat pulse; and
   an injection port positioned to receive the carrier gas from the desorption port, the injection port capable of being heated by a heat pulse, wherein the molecules of interest is positioned between the desorption port and the injection port, the sample particles having the molecules of interest being heated as the heated carrier gas exits the desorption port and enters the injection port, the heated carrier gas further causing the molecules of interest to release a vapor into the injection port.

3. The system as claimed in claim 2, wherein the gas column device has a first portion and a second portion, the first portion positioned inside the injection port, the second portion positioned outside the injection port, wherein the carrier gas carrying the vapor of the molecules of interest is transported from the first portion to the second portion.

4. The system as claimed in claim 3, wherein the detector is connected to the second portion.

5. The system as claimed in claim 4, wherein the detector is a cold ion mobility spectrometer for ionizing the individual components of the molecules of interest.

6. The system as claimed in claim 5, wherein the cold ion mobility spectrometer comprises:
   an inlet port for inputting individual components of the molecules of interest to be detected;
   a first reaction region structure for receiving the individual components of the molecules of interest, the inlet port at a temperature greater than a temperature of the reaction region;
   an ionization source for ionizing selected molecules of the individual components of the molecules of interest to be detected;
   means for transporting the ionized selected molecules across a drift region for subsequent detection,
   whereby remaining individual components of the molecules of interest introduced into the reaction region condense in the reaction region after their introduction therein to effectively eliminate sample vapors and further ionization reactions thereof in the IMS.

7. The system as claimed in claim 6, wherein the system further includes:
   a computer controller for controlling heat pulse sequences; and
   an amplifier connected to the detector for amplifying signals generated by the ionized components for further signal processing by the computer controller.

8. The system as claimed in claim 7, wherein the system further includes an output device for presenting the signals processed.

9. The system as claimed in claim 8, wherein the system is enclosed in a portable hand-held case.

10. The system as claimed in claim 1, wherein the gas column device further includes a metallic jacket capable of being directly heated by passing a current through the metallic jacket.

11. The system as claimed in claim 2, wherein the system further includes a first heater capable of transmitting pulsed heat to the desorption port.

12. The system as claimed in claim 2, wherein the system further includes a second heater capable of transmitting pulsed heat to the injection port.

13. The system as claimed in claim 2, wherein the system further includes a third heater capable of transmitting pulsed heat to the gas column device.

14. The system as claimed in claim 2, wherein the system further includes:
   a nozzle for inputting the sample particles having molecules of interest to be collected and vaporized for detection, the nozzle having a first end where the sample particles having the molecules of interest is inputted, the nozzle further having a second end;
   a pump tube attachable to the second end of the nozzle;
   a ribbon passing between the nozzle and the pump tube, the ribbon for collecting the sample particles having the molecules of interest at the first position,
   wherein the sample particles having the molecules of interest are sucked through the nozzle onto the ribbon by the pump tube, the ribbon having the sample particles having the molecules of interest further moved along to be positioned between the desorption port and the injection port at the second position.

15. The system as claimed in claim 14, wherein the ribbon is a porous type.

16. The system as claimed in claim 14, wherein the ribbon is a metallic mesh.

17. A method for high speed sampling and analysis of molecular components in a gas chromatographic separation system, the method comprising:
   receiving sample particles having molecules of interest at a port device;
   heating the port device to a selected temperature to transform the molecules of interest into a vapor;
   moving the vapor to a gas column device having a temperature less than the port device;
   condensing the vapor in the gas column device;
   heating the gas column device with a heat pulse to a predetermined temperature to cause the vapor to separate into individual components which exit the gas column at different times.

18. The method as claimed in claim 17, wherein the method further includes:
   receiving the individual components into a detector device when the individual components exit the gas column device.

19. The method as claimed in claim 18, wherein the method further includes:
   inputting the individual components into a reaction region of the detector device, the individual components being input to the device via an input port;
   heating the input port to a temperature greater than a temperature of the reaction region;
   ionizing selected molecules of the individual components;
   transporting the ionized selected molecules across a drift region for subsequent detection; and
   condensing remaining individual components in the reaction region after their introduction therein to effectively eliminate the individual components and further ionization reactions thereof in the IMS.

20. The method as claimed in claim 19, wherein the method further includes:
   collecting the sample particles having the molecules of interest onto a ribbon from an input nozzle before the step of receiving.

* * * * *